United States Patent [19]

Hassler

[11] 4,127,842
[45] Nov. 28, 1978

[54] APPARATUS FOR THE MEASUREMENT OF FLOWING MEDIA ACCORDING TO THE ULTRASONIC DOPPLER METHOD

[75] Inventor: Dieter Hassler, Erlangen, Germany

[73] Assignee: Siemens Aktiengesellschaft, Berlin & Munich, Germany

[21] Appl. No.: 742,666

[22] Filed: Nov. 17, 1976

[30] Foreign Application Priority Data

Dec. 8, 1975 [DE] Fed. Rep. of Germany ....... 2555134

[51] Int. Cl.$^2$ .......................... G01S 9/66; A61B 10/00
[52] U.S. Cl. .................................. 340/3 D; 73/194 A; 128/2.05 F; 128/2.05 Z
[58] Field of Search ..................... 340/3 D; 73/194 A; 128/2.05 F, 2.05 Z

[56] References Cited

U.S. PATENT DOCUMENTS

| | | | |
|---|---|---|---|
| 2,859,433 | 11/1958 | Saxton et al. ........................ | 340/3 D |
| 3,541,499 | 11/1970 | Lange .................................. | 340/3 D |
| 3,554,030 | 1/1971 | Peronneau ......................... | 73/194 A |

Primary Examiner—Richard A. Farley
Attorney, Agent, or Firm—Hill, Gross, Simpson, Van Santen, Steadman, Chiara & Simpson

[57] ABSTRACT

To compensate the Doppler flow measurement for the angle of the ultrasonic beam relative to the flowing medium, the ultrasonic applicator includes a mechanical electrical angular position sensor for generating a signal as the applicator is shifted from a perpendicular relationship to the flow axis to a desired oblique angular relationship. As a particularly preferred embodiment, a rotary member is held relative to the flow axis as the applicator axis is rotated, placing a strain gauge under a proportional tension to unbalance a bridge circuit. A further development provides a sensor output as a function of the cosine of the angle of interest so that the bridge output is in the form required to compensate the flow measurement signal without a prior trigonometric operation thereon.

14 Claims, 2 Drawing Figures

APPARATUS FOR THE MEASUREMENT OF FLOWING MEDIA ACCORDING TO THE ULTRASONIC DOPPLER METHOD

BACKGROUND OF THE INVENTION

This invention concerns an apparatus for the measurement of flow rate of a flowing medium according to the ultrasonic Doppler method, which apparatus comprises an applicator with an ultrasonic generator and Doppler processing means for providing a Doppler flow measurement compensated for the ultrasonic radiation angle relative to the flow axis of the flowing medium.

In the case of flow measurements of flowing media, what is of primary interest is the velocity of flow or also the volume rate of flow, the latter, however, being readily calculated by means of product formation if the velocity of flow and the flow cross section are known. In all these measurements, however, there is the disadvantage that the frequency of the received Doppler signals which are used as the criterion for the velocity of flow, is not, as is actually desired, solely dependent upon the flow rate since this frequency is also dependent upon the irradiation angle of the ultrasonic energy relative to the flow axis of the flowing medium. In U.S. Letter Pat. No. 3,766,517, there is shown a prior art apparatus for the angle-independent measurement of flow rate, particularly that of the blood, wherein by means of the irradiation of ultrasonic energy from two transmission directions forming an angle of 90°, the effect of the angle between the irradiation axis and the flow axis is eliminated. Thus if the angles are designated $\alpha$ and 90 minus $\alpha$, the frequency shifts $\Delta f_1$ and $\Delta f_2$ due to the Doppler effect are equal to $k \cos \alpha$, and $k \cos(90-\alpha)$ or $k \sin \alpha$. If the signals $\Delta f_1$ and $\Delta f_2$ are squared and then summed, in suitable signal processing circuitry, the result may be expressed as: $\Delta f_1^2 + \Delta f_2^2 = k^2(\sin^2\alpha + \cos^2\alpha)$. In this expression the radiation angle $\alpha$ is eliminated since $\sin^2\alpha + \cos^2\alpha$ is equal to one. In addition, there is another prior art apparatus for the angle-independent measurement of flow rate, particularly of the blood, where two transmitter/receiver elements are arranged at a specific interval next to one another, and the time difference between the arrival of the ultrasonic energy at the first and second transmitter/receiver elements after impingement on the flowing medium is measured. (In this latter apparatus, the ultrasonic energy is radiated into the medium from the two sources simultaneously, and the time difference $\Delta t$ is measured. The angle correction value $k$ is calculated according to the equation $$k = \frac{1}{\cos\alpha} = \sqrt{1 + \left(\frac{2a}{c \Delta t}\right)^2}$$

where $c$ represents the velocity of the ultrasonic energy, and $a$ represents the interval between the two transmitter/receiver elements.)

Both apparatus do indeed render possible an exact angle-independent measurement; however, they have the disadvantage that the angle-independence is achieved with relatively high electronic processing expenditures.

SUMMARY OF THE INVENTION

It is an object of the present invention to disclose an apparatus of the type initially cited which permits the angle independent measurement of flow with technically simpler means.

As specified by the invention, this problem is solved with a mechanical angle position sensor assigned to the applicator which is actuated in accordance with the angular position of the applicator, the mechanical angular position sensor being equipped with a mechanical/electrical transducer for producing electric angle signals corresponding to the angular position detected by the sensor, and a difference forming means for forming a difference signal as a function of the angle signals.

The apparatus according to the invention permits the determination of the irradiation angle, or of a value dependent upon the irradiation angle, with the simplest technical means in such a manner that an angle-signal is first ascertained during perpendicular irradiation of the ultrasonic energy relative to the axis of the flowing medium. As is known, this perpendicular orientation can be established by locating the minimum of the Doppler flow reading as a function of angle of irradiation. Subsequently, the angle signal obtained at a desired inclination of the applicator is subtracted from the angle signal obtained for the perpendicular orientation. The differential signal then represents a direct cirterion for the angle deviation of the ultrasonic beam direction from the perpendicular and thus also represents a criterion for the irradiation angle of the ultrasonic energy into the flowing medium. (If the irradiation angle is designated by $\alpha$, a differential signal results which is proportional to 90° minus $\alpha$.) The differential angle signal so obtained can then be used directly for the purpose of correcting the Doppler signals so as to obtain an angle independent flow measurement. For a direct determination of the differential signal, a preferred embodiment of the invention specifies that the transducer is to be part of a measuring bridge circuit which is balanced in the case of angle signals with the applicator in an orientation corresponding to a minimum of the flow reading. Then, with the applicator in a desired angular orientation, the measuring bridge circuit is unbalanced so as to provide a signal difference formation as a function of the orientation. The angular position sensor itself can be operated by gravitational force and can provide an actuation of an ohmic, capacitive, or inductive transducer automatically according to the inclination of the applicator axis relative to the vertical. Such a gravity type angle position sensor and transducer assembly can be completely contained within an applicator housing which carries the ultrasonic transducer, and other components of the processing circuitry can also be contained within the housing to the extent this is convenient. In addition to weighted or gravity type transducers, for example of the resistance or rotary potentiometer type, so-called liquid level potentiometers with mercury, for example, as the liquid slider also enter into consideration as ohmic angle transducers. Weighted or gravity type variable capacitors are suitable as capacitive angle indicators, and mutually adjustable coils, one of which is weighted, are suitable as inductive angle transducers. However, a technically especially simple construction of an angle position sensor with the smallest space requirement results from the introduction of a mechanical tilting/rotary converter which converts the tilting movements of the applicator into corresponding rotary movements of a rotary member. By way of example, a tension element, such as a wire bow, for example, or the like, may serve as the torque generator for producing rotary movement of the rotary member relative to the applicator. A wire bow, for example, may engage the rotary member during the tilting movement of the applicator so as to retain the rotary member at a fixed angular relationship to the flow axis of the flowing medium. The mechanical/electrical transducer is then preferably a resistance which is sensitive to stress, for example tension or bending, such as a wire resistance strain gauge element which is mounted by means of a tension spring between the rotary member on the one hand and the applicator housing on the other hand such that the stress applied to the strain gauge element is proportional to the relative rotary motion of the rotary member.

Other objects features and advantages of the invention will be apparent from the following detailed description of two illustrative embodiments when taken in connection with the accompanying drawings.

DETAILED DESCRIPTION

Figure 1:
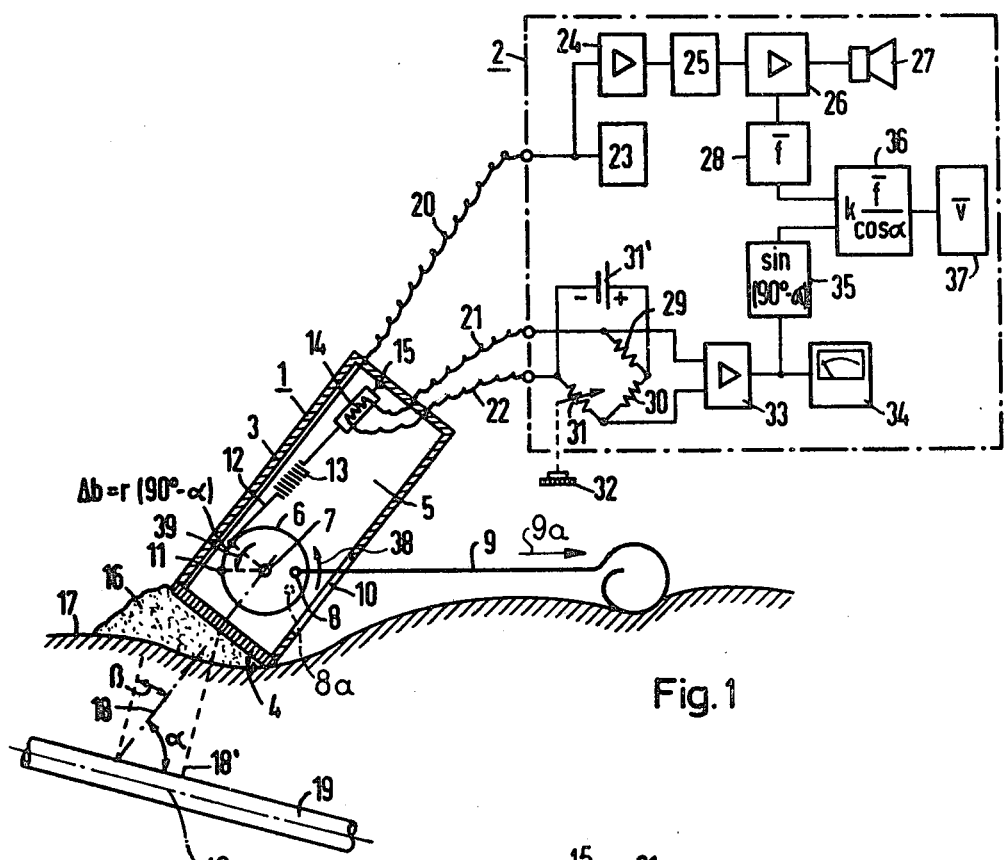
FIG. 1 illustrates the fundamental construction of an apparatus according to the present invention, with an ultrasonic applicator shown in longitudinal section.

In FIG. 1, reference numeral 1 designates an ultrasonic Doppler applicator having Doppler processing means associated therewith including circuitry 2 for providing a Doppler flow measurement. Applicator 1 consists of a carrier section or applicator housing 3 for carrying ultrasonic vibrator means 4. By way of example, ultrasonic means 4 may comprise a small piezoelectric crystal plate. The applicator housing has an interior hollow space 5 with a rotary member 6 or circular configuration rotatably supported in such space by means of an axle 7. On the rotary member or wheel 6 is a mechanical engagement means 8 for coupling with a wire bow 9. In the illustrated embodiment, the wire bow 9 is under tension so as to exert a force in the direction of arrow 9a on the engagement means 8. In the illustrated embodiment, the force exerted by tension member 9 is sufficient to hold engagement point 8 at the circumference of wheel 6 at a fixed angular relationship in spite of any tilting movement of the applicator 1. Thus, as illustrated in FIG. 1, the engagement point 8 is in alignment with the axis 7 with respect to the direction of the tension force as indicated by arrow 9a. The wire bow 9 is guided from the interior space 5 to the exterior via a through passage slot 10 in applicator housing 3. Diametrically opposite to engagement means 8 is a second engagement means 11 at the circumference of wheel 6, and a tension spring 13 is indicated as being coupled with the second engagement means 11 via a draw thread 12. The rotary member 6 in conjunction with the orientation maintaining means 9 provides a mechanical angular position sensor or a mechanical tilting/rotary converter for converting the tilting movements of the applicator 1 into a tension force. Associated with the mechanical means is a mechanical/electrical transducer such as wire resistance strain gauge 14 shown connected between tension spring 13 and a fixed point 15 on applicator housing 3. The electrical transducer means responds to the actuation of the mechanical means in accordance with the varying angular positions of the applicator 1 to produce a corresponding change in stress on the electrical transducer means 14 so as to produce a angle responsive signal in the form of a varying impedance of the transducer means as a function of the angle of the applicator 1. The wire resistance strain gauge 14, for example, can also be directly applied to the windings of tension spring 13; for example it can be fixed onto the successive turns of the tension spring 13 by means of an adhesive. In the illustrated embodiment according to FIG. 1, the applicator 1 with ultrasonic vibrator means 4 is coupled to the skin surface 17 of a patient, for example to the upper arm of the patient, via a coupling gel 16 such that, in the operating state, the ultrasonic means may be operated to transmit a beam of ultrasonic energy along the applicator axis 18 so as to impinge on a blood vessel 19 extending beneath the skin surface. The irradiation angle of the ultrasonic energy relative to the flow axis 19a within the blood vessel is designated by $\alpha$. The angle $\beta$ designates the angle between the normal line 18' which coincides with the applicator axis during perpendicular irradiation of ultrasonic energy into the blood vessel 19 and the illustrated inclined position of the applicator 1.

In the exemplary embodiment according to FIG. 1, applicator 1 is additionally connected to Doppler processing circuit 2 via connecting lines 20, 21 and 22 (which, in a practical embodiment, could extend via a common multiconductor cable). Line 20 indicates the connecting line for the connection of ultrasonic vibrator means 4 to the transmitter and receiver section of the Doppler circuit. The transmitter section consists of a high frequency oscillator 23 which supplies ultrasonic means 4 with high frequency impulses each comprising a wave of the desired ultrasonic transmitting frequency so as to operate the means 4 as an ultrasonic generator. The ultrasonic energy is transmitted essentially along the applicator axis 18 so as to impinge on the flowing medium within the conduit 19. The receiving section consists of a receiving amplifier 24 for receiving the ultrasonic echo signals after impingement on the flowing medium, a Doppler demodulator 25 for receiving the Doppler signals, as well as a low frequency amplifier 26 for the Doppler signals. The Doppler signals obtained at the output of the low frequency amplifier 26 can be made audible by means of a loudspeaker 27. Low frequency amplifier 26 is further connected to a mean value circuit 28 via an additional output. This mean value circuit is, for example, constructed corresponding to that of U.S. Letters Patent No. 3,675,192 and determines a weighted mean value $\bar{f}$ of the Doppler frequency from the received low frequency Doppler signals.

Connection lines 21 and 22 connect wire resistance strain gauge element 14 as a variable resistance into an ohmic resistance (Wheatstone) bridge consisting of additional resistances 29, 30 and 31, as well as a voltage source 31'. Of the cited resistances, resistance 31 is an ohmic resistance potentiometer which is adjustable by means of a knob 32. The bridge output terminals are connected to the input of an amplifier 33 which receives a bridge signal as a function of the unbalance of the bridge. The amplifier 33 is, in turn, connected at its output side with a needle type indicating meter 34 which thus provides a visual indication of the amplitude of the bridge output signal and which can also be calibrated in angular degrees so as to represent the angle $\beta$ as illustrated in FIG. 1. In addition, a sine/cosine forming circuit 35 is connected to the output of amplifier 33 and is operable for calculating the cosine of the irradiation angle on the basis of the output signal of amplifier 33. In particular the output from amplifier 33 is proportional to 90° minus $\alpha$, and circuit 35 in providing an output according to the sine of (90° minus $\alpha$) thus provides an output which is a function of the cosine of $\alpha$. The cosine value calculated in this manner is delivered by the sine/cosine 35 to a dividing circuit 36, to which the output signal from the mean frequency circuit 28 is supplied via a second input for the purpose of forming a quotient signal in accordance with $k$.

$$\frac{\bar{f}}{\cos\alpha}.$$

The constant $k = c/2f_o$ where $c$ represents the ultrasonic velocity and $f_o$ is the ultrasonic transmitting frequency. The quotient from dividing circuit 36 thus represents a direct measured value for the mean flow velocity $\bar{v}$ for the blood flowing in vein 19, and an indicator is indicated at 37 for the purpose of indicating the velocity value $\bar{v}$ which has been determined in this manner.

The mode of operation of the exemplary embodiment according to FIG. 1 will be apparent with regard to the determination of the irradiation angle as well as the subsequent angle direction of the Doppler signal, from the following description:

First, the approximate course of blood vessel 19 beneath the skin surface 17 is ascertained by means of scanning the body surface at three or four points located one behind the other, in conjunction with rendering of the Doppler signals acoustically audible. The connection line between the scanning points is marked on skin 17 by means of a chalk stroke. Subsequently, draw wire 9 is placed on the skin parallel to the direction of this stroke in a taut manner and fixed in position for example by means of an adhesive plaster. The actual angle measurement is now begun. During Doppler indication by means of loudspeaker 27, applicator 1 is slightly tilted over an angle such that the Doppler indication passes through a minimum. Upon passing through such minimum, the ultrasonic transmitting-/receiving beam from ultrasonic vibrator means 4 has its axis 18 aimed in a direct perpendicular direction intersecting blood vessel 19 (the beam path corresponding to that indicated at 18' by means of a broken line in FIG. 1.) In this position, that is with a minimum Doppler indication, potentiometer 31 may be manually adjusted by means of rotary knob 32 in such a manner that the bridge output signal becomes zero (the bridge is balanced). Subsequently, while the wire bow 9 continues to be held taut, applicator 1 is, for example, brought into the illustrated tilted position with its axis 18 forming the angle $\alpha$ with flow axis 19a of the blood stream within vein 19. However, tilting of applicator 1 while maintaining bow 9 taut during the angular adjustment of applicator 1 through the angle $\beta$ as illustrated in FIG. 1, causes point 8 to rotate about axle 7 from an initial position as indicated at 8a to the position 8 relative to the housing. Actually, in the illustrated embodiment, the tension of bow 9 acting in the direction of arrow 9a serves to maintain rotary member 6 in the orientation shown in FIG. 1 relative to the blood flow axis 19a as the applicator 1 is turned in a clockwise direction about the axle 7 and through an angle as indicated at $\beta$, the applicator axis shifting from a direction parallel to line 18' to a direction coincident with the axial line 18. The corresponding relative rotation of rotary member 6 relative to the applicator housing 3 is indicated by arrow 38 in FIG. 1. This same relative rotation of member 6 causes engagement means 11 for the draw thread 12 on the opposite side of member 6 to be displaced by an amount $\Delta b$ in the relative direction represented by arrow 39. By way of example, the arrangement may be such that when engagement means 11 is located on a radius arm disposed at right angle to the applicator axis 18, spring 13 will be entirely unloaded, and the bridge 29-31 in the present example will thus have been balanced for a case of essentially zero tension exerted on the strain gauge 14. Then, as housing 3 is rotated from an orientation parallel to line 18' to the orientation shown in FIG. 1, spring 13 will be extended by an amount $\Delta b$ and the corresponding tensioning of the wire resistance strain gauge 14 provides a signal in the form of a resistance change which is communicated to resistance bridge 29, 30, 31 of the processing circuitry 2. The result is that the bridge will then be out of balance and will deliver at its bridge output an electric voltage signal corresponding to the degree of bridge unbalance. Since the relative angular rotation of rotary member 6 corresponds precisely to the tilt angle $\beta$ of ultrasonic applicator 1 from an orientation parallel to line 18', the signal from strain gauge 14 will be proportional to the product of the radius distance $r$ to engagement point 11 multiplied by the angle $\beta$ in radians. If the angle $\beta$ is converted to the actual irradiation angle $\alpha$ as indicated in FIG. 1, the result is indicated by the equation $$\Delta b = r(\frac{\pi}{2} - \alpha).$$

Since the change in the tension on wire resistance strain gauge 14 and thus its resistance change is directly proportional to the arc length $\Delta b$, a voltage signal results at the output of bridge amplifier 33 which is directly proportional to 90° minus $\alpha$. From this, the desired correction value for the irradiation angle during Doppler signal reading, namely a signal in accordance with cosine $\alpha$ is obtained at the output of sine/cosine circuit 35 since the function sin $$(\frac{\pi}{2} - \alpha) = \cos\alpha.$$

Figure 2:
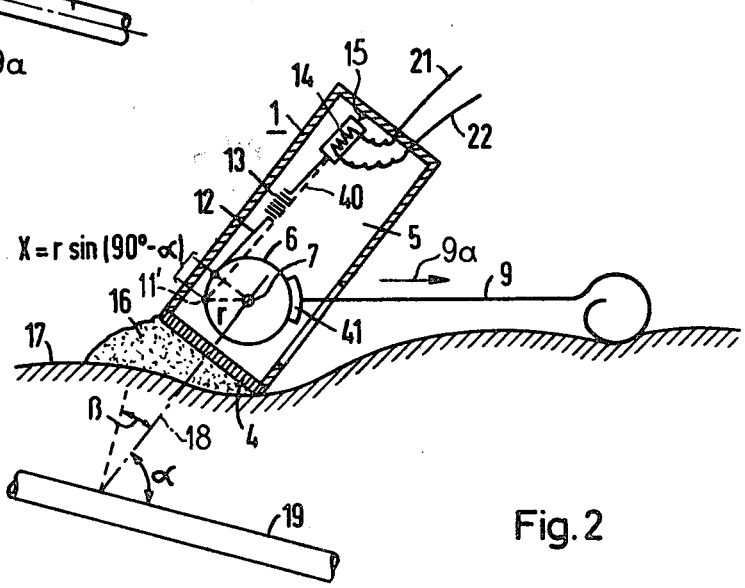
FIG. 2 illustrates a modification of the applicator arrangement of FIG. 1.

Thus in the exemplary embodiment according to FIG. 1, a tensile load or a corresponding resistance change in wire resistance strain gauge 14 is obtained which is directly proportional to $\pi/2 - \alpha$. Only by means of the sine conversion in circuit 35 is the desired function of cosine $\alpha$ then obtained. However, this cosine $\alpha$ signal can also be directly determined without the connection of a sine forming circuit by means of a simple modification of the tilting/rotary converter of the applicator according to FIG. 1. As illustrated in FIG. 2, the draw thread 12 for tension spring 13 proceeds to a coupling means 11' which is not centered at the peripheral surface of rotary member 6 but is located to one axial side of the peripheral surface so that the thread 12 will extend along a straight line from point 15 to coupling means 11' as indicated by the dash connecting straight line 40. Thus, while in FIG. 1, the thread 12 is wrapped on the circular circumferential surface of rotary member 6; in FIG. 2, the thread 12 is to one side of rotary member 6 so as to follow a path as indicated at 40 in FIG. 2 as the housing of applicator 1 is rotated through an angle β in the clockwise direction to the orientation shown. Thus, the position of thread 12 shown in solid outline in FIG. 2 is the position of the thread relative to the housing of the applicator when the applicator axis is perpendicular to the direction of blood flow within the vessel 19. From the initial position shown in solid lines for thread 12, the thread is moved a distance parallel to the applicator axis 18 designated by the letter x, where $$x = r \cdot \sin(\frac{\pi}{2} - \alpha).$$

Thus, with the coupling means 11' at the position shown in FIG. 2, when the applicator has been brought into the tilt position having the irradiation angle α, the path change for the draw thread 12 no longer corresponds to the arc Δb as in FIG. 1; on the contrary, the path change corresponds to the path segment $$x = r \cdot \sin(\frac{\pi}{2} - \alpha).$$

Accordingly in FIG. 2 a resistance change results for the wire strain gauge 14 which is proportional to sine $$(\frac{\pi}{2} - \alpha),$$

that is proportional to cosine α. Thus for the embodiment of FIG. 2, the output of bridge amplifier 33 and the reading at indicator 34 is proportional to cosine α, and this output is connected directly to the second input of the quotient forming circuit 36. Thus in the exemplary embodiment according to FIG. 2, the formation of the function cosine α is not effected electronically in the Doppler processing circuit 2, but is carried out mechanically by means of the tilt/rotary converter of the applicator of FIG. 2. Moreover, in an additional modification in FIG. 2, the wire bow 9 for the applicator according to FIG. 2 is coupled to rotary member 6 via a detachable coupling 41 which may be in the form of a button secured at the periphery of wheel 6 and a coupling socket member 41 which can be detachably snapped onto such button, for example, in a structure which may be entirely similar to a conventional "snap fastener", for example. Thus, in the embodiment of FIG. 2, the bridge circuit 29, 30, 31 is first balanced to provide a zero output reading with the applicator housing having its axis 18 perpendicular to the flow axis such as 19a in the vessel 19. At this time the draw bow 9 will be under tension and will be coupled with the rotary member 6 by means of the detachable coupling 41, for example so as to hold the draw thread 12 in the position shown in solid outline in FIG. 2, the coupling means 11' being located on a radius line which extends at right angles to the applicator axis 18, for example, and the tension spring 13, in this position, having essentially zero tension. After the minimum of the flow indication has been located and the bridge balanced for this orientation, the applicator housing is rotated in the clockwise direction through the angle β, and the ultrasonic vibrator means 4 is coupled with the skin surface 17 by means of a coupling gel 16 as in the embodiment of FIG. 1. Since the wire bow 9 need not be fastened to the rotary member 6 during location of the perpendicular irradiation position, handling of the applicator housing during this phase is facilitated. Thus, the approximate course of blood vessel 19 beneath the skin surface 17 may be ascertained with draw bow 9 detached, and with essentially a zero tension of spring 13 and a zero tensioning of strain gauge 14. Thus with the angle α equal to 90°, the output of bridge amplifier 33 for the embodiment of FIG. 2 will be essentially zero, and there is no need for adjusting of the bridge circuit because of an initial angle of rotary member 6 providing an initial stress on the strain gauge 14, prior to the actual rotation of the applicator housing from the perpendicular orientation to the orientation shown in FIG. 2.

While several presently preferred embodiments of the invention have been illustrated by way of example and not by way of limitation, it will be apparent that many modifications and variations may be effected without departing from the scope of the novel concepts of the present invention.

I claim as my invention:

1. In apparatus for measuring the flow of flowing media according to the ultrasonic Doppler effect method, including an applicator having ultrasonic vibrator means for the reception of ultrasonic energy substantially along an applicator axis after impingement on a flowing medium having a given flow axis, and Doppler processing means coupled with said ultrasonic vibrator means for processing signals in accordance with the ultrasonic energy as received by the applicator and in accordance with the angle of the applicator axis relative to the flow axis of a flowing medium to provide a Doppler flow measurement of a flowing medium independently of the angle formed between the applicator axis and the flow axis of such flowing medium, said processing means including a mechanical angular position sensor for sensing the angle of the applicator axis and comprising mechanical means for actuation in accordance with varying angular positions of the applicator, and mechanical/electrical transducer means responsive to actuation of the mechanical means to provide electrical angle responsive signals corresponding to the angular positions of said applicator, said mechanical angular position sensor comprising a mechanical tilt/rotary converter with said mechanical means comprising a rotary member rotatably carried by said applicator, and engaging means for mounting at an application location and engaging the rotary member so as to maintain the rotary member in a fixed angular orientation relative to the flow axis during tilting movement of the applicator, the applicator axis thereby rotating relative to the axis of the rotary member as the applicator is tilted.

2. Apparatus according to claim 1 with said mechanical/electrical transducer means comprising a resistance which is sensitive to stress and is coupled between the applicator and the rotary member such that the resistance is stressed in proportion to the relative rotary movement of the rotary member with reference to the applicator axis.

3. Apparatus according to claim 1 with said rotary member being of circular configuration and having an axis of rotation essentially intersecting the applicator axis.

4. Apparatus according to claim 3 with the means for holding the rotary member against rotation comprising a tension element engagable at the periphery of said rotary member and serving to exert a tension force substantially on a line with the axis of rotation of said rotary member.

5. Apparatus according to claim 4 with said tension element comprising a wire bow engaging at the circumference of the rotary member at a first point, and the mechanical/electrical transducer means being coupled with the rotary element at a second point substantially diametrically opposite to said first point.

6. Apparatus according to claim 4 with said mechanical/electrical transducer means being coupled with the rotary member by means of a draw thread which runs along the circumference of the rotary member to said second point.

7. Apparatus according to claim 5 with said mechanical/electrical transducer means being coupled to said rotary member via a draw thread which extends along a connecting straight line intersecting the circumference of the rotary member at said second point.

8. Apparatus according to claim 1 with said rotary member having a detachable coupling with said last mentioned means.

9. Apparatus according to claim 1 with said applicator comprising an applicator housing containing said rotary member and said mechanical/electrical transducer means, and said applicator housing having a through passage slot for receiving said engaging means which is to be engaged with said rotary member.

10. Apparatus according to claim 1 with said processing means comprising a difference formation circuit connected with said transducer means and adjustable to provide a null signal when the applicator axis is substantially perpendicular to the flow axis of a flowing medium and thereafter operable to provide a differential signal as a function of the tilting of the applicator axis away from the perpendicular orientation.

11. In apparatus for measuring the flow of flowing media according to the ultrasonic Doppler effect method, including an applicator having ultrasonic vibrator means for the reception of ultrasonic energy substantially along an applicator axis after impingement on a flowing medium having a given flow axis, and Doppler processing means coupled with said ultrasonic vibrator means for processing signals in accordance with the ultrasonic energy as received by the applicator, said processing means including a mechanical angular position sensor for sensing the angle of the applicator axis and comprising mechanical means for actuation in accordance with varying angular positions of the applicator, and mechanical/electrical transducer means responsive to actuation of the mechanical means to provide electrical angle responsive signals corresponding to the angular positions of said applicator, a method of operating said apparatus to enable a Doppler flow measurement independently of the angle formed between the applicator axis and the flow axis, comprising the steps of:
(a) orienting the applicator axis relative to the flow axis of the flowing medium, and obtaining a first electrical angle responsive signal during substantially perpendicular irradiation of the ultrasonic energy relative to the flow axis,
(b) orienting the applicator axis at a desired inclination to the flow axis, and obtaining a second electrical angle responsive signal during irradiation of the flow axis at an oblique angle, and
(c) forming a differential signal based on the difference between the second electrical angle responsive signal and the first electrical angle responsive signal, as a direct criterion for the angle deviation of the ultrasonic beam from the perpendicular, whereby a Doppler flow measurement carried out at the oblique angle can be obtained independent of the ultrasonic radiation angle relative to the flow axis.

12. The method of claim 11, wherein the differential signal is formed by connecting a difference formation circuit with the mechanical/electrical transducer means, and adjusting the difference formation circuit to provide a null signal when the applicator axis is substantially perpendicular to the flow axis, so that the difference formation circuit thereafter provides the differential signal as a function of the tilting of the applicator axis away from the perpendicular orientation.

13. The method of claim 11 wherein the differential signal is formed by connecting a measuring resistance bridge circuit so as to include the transducer means, balancing the bridge for the case of an applicator axis angle corresponding to a minimum Doppler-flow measurement, so that the bridge becomes unbalanced as a function of the applicator axis angle and provides the differential signal relative to the signal from the bridge circuit in the balanced condition thereof.

14. The method of claim 11 wherein the mechanical means comprises a rotary member carried by said applicator, which rotary member is maintained at essentially a predetermined orientation relative to the flow axis during step (b) by coupling the rotary member with a body surface of the body containing said flowing medium, thereby to actuate the transducer means which is connected between the rotary member and the applicator housing.

* * * * *